United States Patent [19]

Horn

[11] 4,000,737
[45] Jan. 4, 1977

[54] SURGICAL INCISION SHIELD

[76] Inventor: Clifford V. Horn, 457 Lakeview Way, Redwood City, Calif. 94062

[22] Filed: Oct. 14, 1975

[21] Appl. No.: 621,959

[52] U.S. Cl. ............................................. 128/154
[51] Int. Cl.² ....................................... A61F 13/00
[58] Field of Search ............... 128/132 R, 154, 171, 128/153, 157

[56] References Cited

UNITED STATES PATENTS

D35,417  12/1901  Steinmetz ..................... 128/154 X

FOREIGN PATENTS OR APPLICATIONS

| 1,146,313 | 5/1957 | France ............................. | 128/154 |
| 269,938 | 12/1945 | Switzerland ...................... | 128/154 |
| 21,561 | 10/1901 | United Kingdom ............... | 128/154 |
| 24,352 | 10/1900 | United Kingdom ............... | 128/154 |

Primary Examiner—Lawrence W. Trapp
Attorney, Agent, or Firm—George B. White

[57] ABSTRACT

An inexpensive adjustable protective device for preventing bedding, clothing and the like from touching and/or rubbing upon a recent surgical incision is described. The device includes at least one longitudinal strip composed of a light rigid material such as plastic supported by several separate rigid support legs composed of the same material. The support elements have an adhesive tab at their distal ends adapted to adhere to the skin surface. On one embodiment, the longitudinal strip has a plurality of female receptacles along its length for receiving a male fastening element integral with the support legs. The support strips hold the longitudinal strip in a spaced relationship above the incision site, thus preventing bedding and/or clothing or similar articles from rubbing against or touching the incision site.

The shield is adjustable to incision length by simply cutting or tearing off a suitable length of the longitudinal strip. The resultant structure is positioned over the incision site with the longitudinal strip oriented above and parallel to the incision line.

10 Claims, 10 Drawing Figures

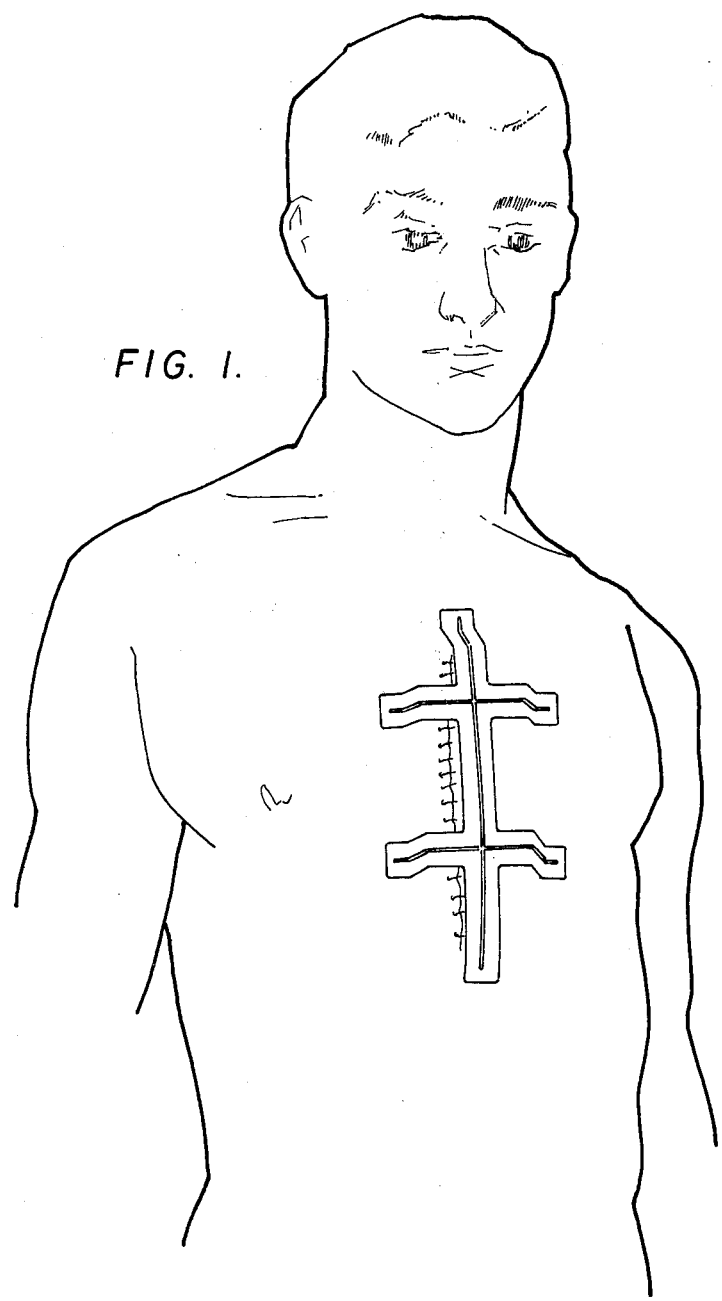
FIG. 1.
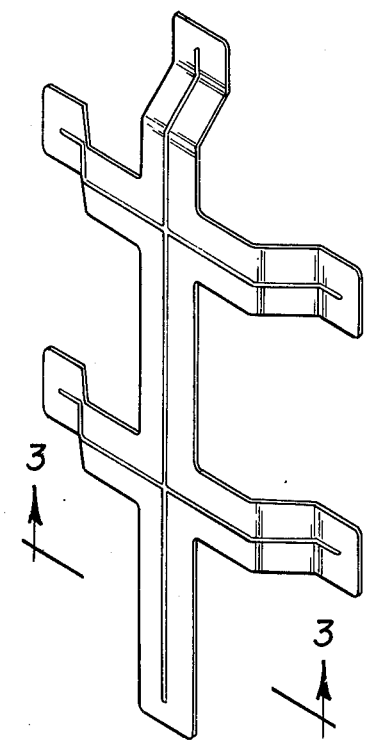
FIG. 2.
FIG. 3.
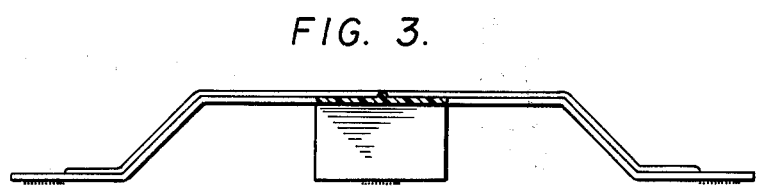
FIG. 4.
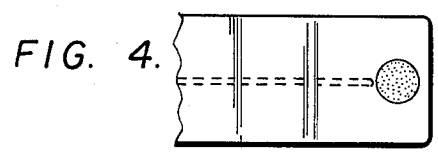

SURGICAL INCISION SHIELD

BACKGROUND OF THE INVENTION

Major surgical procedures such as open-heart surgery often require long incisions into the body cavity to provide adequate access to the treated organ. After the surgical procedure is complete and the incision closed, the incision site usually is not heavily bandaged or otherwise covered up.

Specifically, bandaging and/or gauze placed on an incision site will absorb the moisture and fluid oozing from the closed incision, thus becoming an ideal medium for growth of bacteria and the like. Bandages and gauze also inhibit air circulation around an incision, a factor which slows the healing process.

Bedding, such as sheets and blankets, touching and/or rubbing against an uncovered incision can cause considerable pain and discomfort to a patient. In fact, in many hospitals the bedding is arranged in a tent-like structure such that it will not touch the incision site.

When the patient leaves the hospital he is advised not to bandage or otherwise cover the incision site because of the risk of secondary infection. Accordingly, the patient must face the nightly ordeal of lying in bed hoping nobody moves the bedding and must gingerly move about when dressed to prevent clothing from rubbing across the incision site.

SUMMARY OF THE INVENTION

An inexpensive disposable protective shield is described which prevents bedding, clothing and the like from touching and/or rubbing upon or in the region of a recent surgical incision. The shield consists of at least one longitudinal strip composed of a light structural rigid material such as plastic supported above the incision site by a plurality of support legs. The support legs all have a suitable adhesive at their distal ends adapted to adhere to the skin's surface.

When placed over an incision, the longitudinal strip is aligned parallel to the incision line and the support legs straddle the incision site, to prevent thereby bedding or clothing from coming into contact with or rubbing against the incision site. Since no material is placed against the incision site, air circulates freely, aiding the healing process.

In the simplest embodiment of the incision shield, the longitudinal strip and straddling supports are an integral piece of material which can be cut to incision length.

Also, the longitudinal strip may have a plurality of female snap receptacles along its length, each adapted to snap onto a male button integral with support legs.

Still other objects and advantages of the invented incision shield relates to its simplicity of construction, ease of fabrication and flexibility of use, all of which features will become apparent upon examination of the following detailed description of the basic elements of the invention, together with the accompanying figures.

DESCRIPTION OF THE FIGURES

FIG. 1 shows one configuration of a single piece incision shield in place above a mid-chestline incision on a patient.

FIG. 2 is a perspective view of the incision shield shown in FIG. 1.

FIG. 3 is a cross-sectional view of the incision shield taken along Line 3—3 of FIG. 2.

FIG. 4 is a bottom view of the support leg showing the adhesive pad.

DESCRIPTION OF PREFERRED EMBODIMENTS

Figure 5:
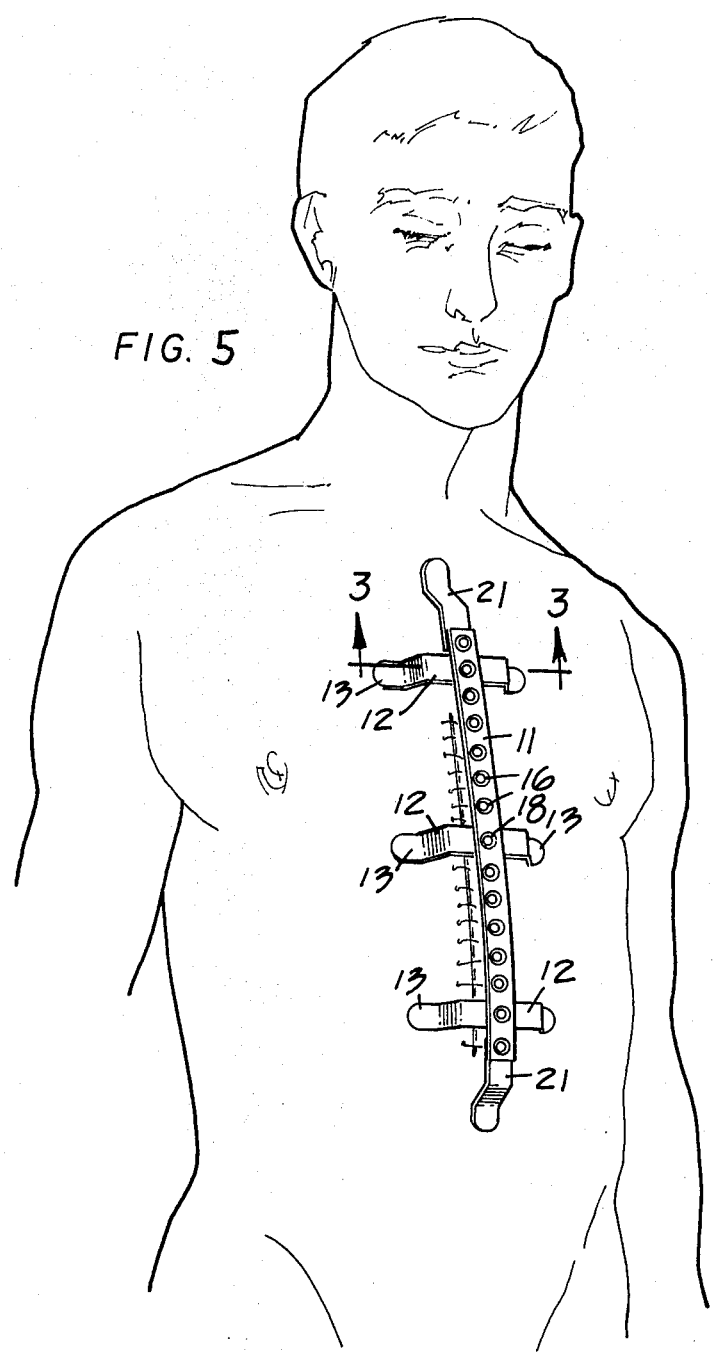
FIG. 5 shows another embodiment of the incision shield, in which the longitudinal strip and support legs are separate pieces.

Referring to FIGS. 1 and 2, a single element incision shield comprises a single integral piece of relatively rigid material 31, such as plastic formed into a longitudinal strip 32 with straddling support legs 33 oriented perpendicularly to said strip.

The support legs form a U-shaped structure and have tabs integrally extending angularly outward from the ends of the legs. As shown in FIG. 4, the tabs have an appropriate adhesive material 35 on their bottom surface which is adapted to adhere to the skin surface.

The longitudinal strip 31 may also have an end support leg 36 with a tab 37 extending therefrom. Rigidity is provided to the unitary structure 31 by a ridge 35 centrally aligned along the top surface of the longitudinal strip 32 and the top surface of the straddling legs 33.

As shown in FIG. 3, the straddling legs 33 support the central strip 32 above and parallel to the incision site. Specifically, the legs 33 straddle the incision site. The combination of the longitudinal strip 32, the straddling legs 33, the end support leg 36, form a stable structure above the incision site to prevent clothing, bedding and the like from rubbing against the incision site. Further, air can circulate freely in and around the incision.

Figure 6:
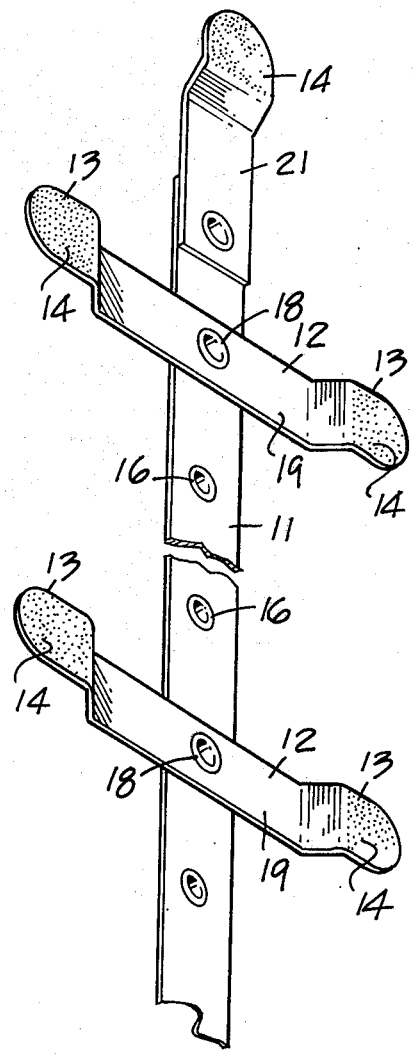
FIG. 6 is an inverted view of the incision shield of FIG. 5.

Referring to FIGS. 5 and 6, the basic elements of a two-element incision shield include at least one longitudinal strip 11 and a plurality of support legs 12, oriented perpendicularly with respect to the strip 11. The longitudinal strip 11 and the support legs 12 may be composed of any light rigid material such as cardboard or stiff plastic material.

The support legs 12 are strips formed into a structural inverted U-shape with tabs 13 integrally extending angularly outward from the legs. The tabs 13 are coated with an appropriate adhesive material 14 adapted to adhere to the skin surface. The longitudinal strip 11 is secured to the support elements 12 by a snap fastener 16 (see FIG. 9).

Figure 8:
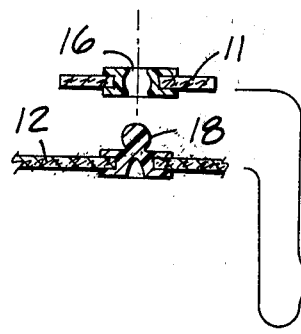
FIG. 8 is an enlarged view showing the snap receptacle-button arrangement for securing the support elements to the longitudinal strip.
Figure 7:
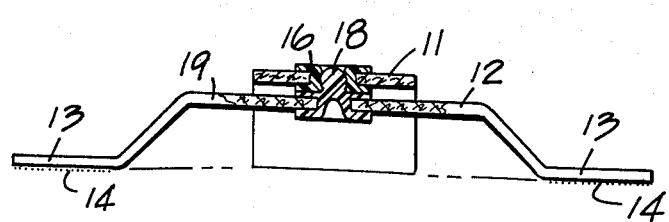
FIG. 7 is a cross-sectional view taken along 8—8 of FIG. 5.

In more detail, referring to FIG. 8, the longitudinal strip has a plurality of snap receptacles 16 along its length, each adapted to receive a snap button 18 mounted centrally on the support bar 19 of the support elements 12. The snap receptacles 16 and snap buttons 18 may be composed of a suitable plastic material or a light metal.

As shown in FIG. 6 the inverted incision protector has two end support elements 21. The end supports 21 are made by simply cutting off one leg of the U-shaped support elements beyond the snap button 18. The remaining leg is secured by the snap receptacle 17 at either end of the longitudinal strip 11 and is aligned with the strip as shown in FIGS. 1 and 2.

Figure 9:
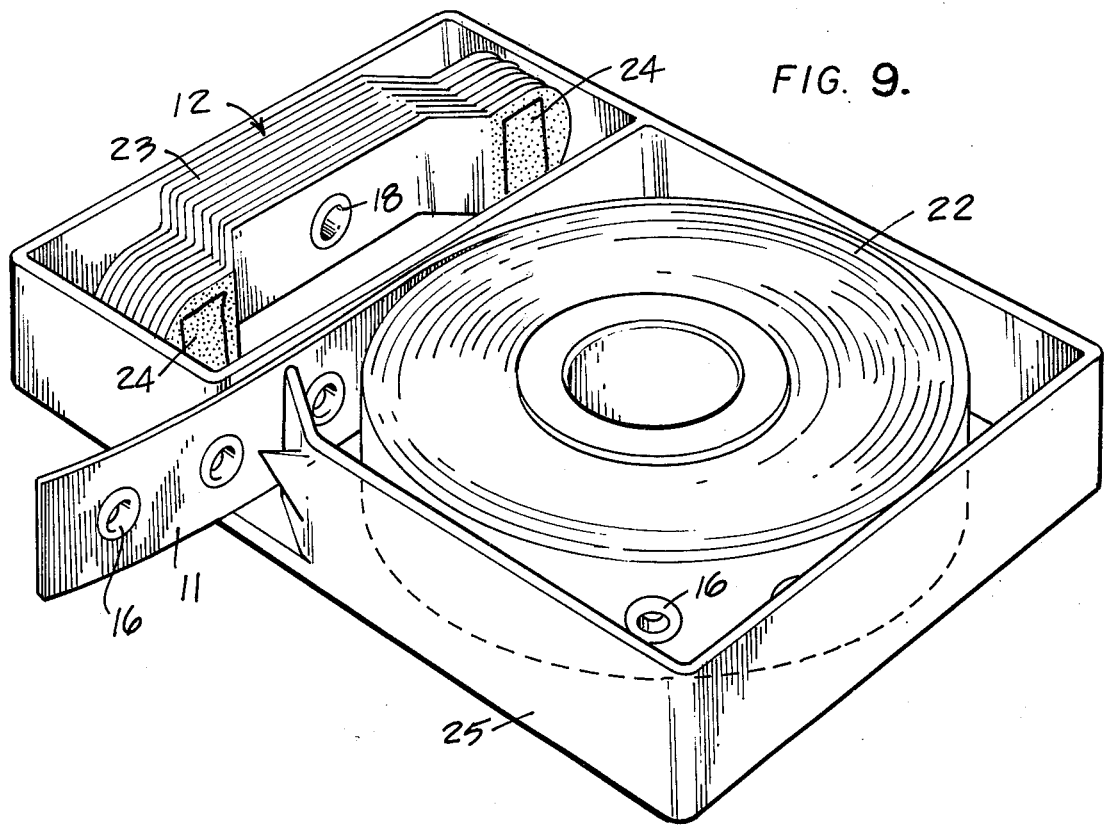
FIG. 9 shows shield components in a dispensing container.

As shown in FIG. 9, the elements of the invented incision shield can be stored separately. Specifically, the longitudinal strip 11 can be stored as a single roll 22. The support legs 12 can be fitted in a nested relationship to form a single stack 23. A suitable membrane 24 covers the adhesive tabs 13 to prevent them from sticking together. The roll 22 of longitudinal strip 11 and the stack 23 of support elements 12 can then be stored in a suitable dispenser container 25 for placement on the shelf.

To fabricate the two-element incision shield, the doctor or the patient simply cuts an appropriate length of the longitudinal strip 11 from the roll 22, snaps an appropriate number of support elements into the receptacles 17 along its length, cuts one leg off of two support elements 12 and snaps them into the snap receptacles 17 at either end of the longitudinal strip. The membrane 24 protecting the adhesive tabs 13 is removed and the patient or doctor then places the resulting structure over the incision site with the longitudinal strip 11 lying parallel to and above the incision line and with the support elements 12 straddling the incision site. (See FIG. 1).

For curved incisions, the longitudinal strip can be bent simply to conform to the incision line. In instances where the incision is sharply curved, two longitudinal strips 11 can be utilized with an appropriate number of support elements. In this case, adhesive tape may be used to secure the adjoining ends of the longitudinal strips 11 together.

Figure 10:
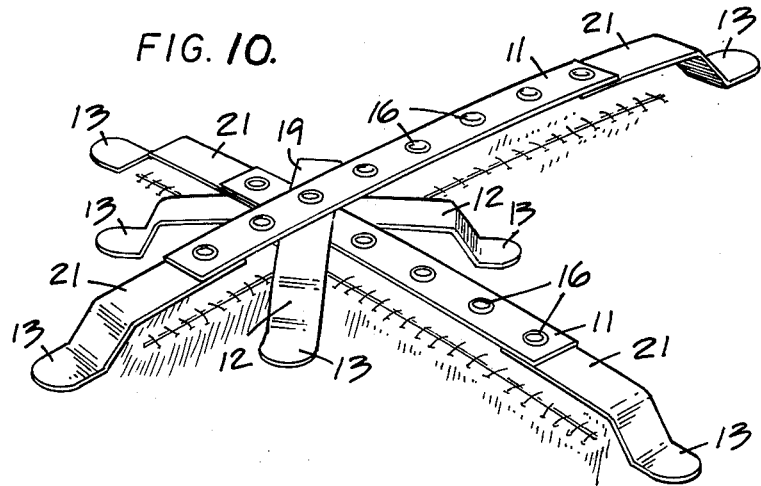
FIG. 10 shows another possible configuration of the incision shield in place over perpendicularly intersecting incisions.

Another example of the flexibility of the described incision shield is illustrated in FIG. 10. Specifically, as depicted in FIG. 10 where two incision lines 31 and 32 perpendicularly intersect, two longitudinal strips 11 are utilized, each parallel to one of the incision lines. At the point of intersection of the longitudinal strip two support elements 12 are used. The first support element 21a is secured to the bottom longitudinal strip and is oriented at an angle 45° with respect to both strips. The second support element 12b is secured to the top longitudinal strip 11 and is oriented at 90° with respect to the support element 12a. In essence, each strip is an independent incision shield that can move laterally with respect to the other. If such lateral movement is not desired then the strips 11 can be secured together with adhesive tape. Additional support elements 12 may be placed as needed along the respective lengths of the two longitudinal strips 11.

While the invented incision shield is described with respect to particular embodiment and configurations, numerous variations and modifications can be effected using the described components of the shield within the spirit and the scope of the invention as described above and as defined and set forth in the appended claims.

I claim:

1. A shield for recent surgical incision sites comprising in combination,
    a longitudinal strip composed of a relatively rigid material,
    a plurality of U-shaped support elements each composed of a relatively rigid material oriented perpendicularly with respect to said longitudinal strip adapted to support said strip above and parallel said incision site, said U-shaped support elements bridging the incision site,
    an end support leg extending from at least one end of said longitudinal strip adapted to support the end of said strip,
    means for securing the distal ends of said U-shaped support elements to the skin surface on each side of the incision site and for securing the distal end of said support leg to the skin surface beyond the end of said incision.

2. The incision shield of claim 1 wherein said longitudinal strip, said U-shaped support elements and said end support leg are composed of the same material and are integral.

3. The incision shield of claim 2 wherein said longitudinal strip, said U-shaped support elements and said end support leg each have an integral ridge of said material aligned centrally along their top surface to provide additional rigidity.

4. The incision shield of claim 3 wherein said means for securing said U-shaped support elements and said end support to the skin surface comprise,
    a plurality of tabs, each integrally extending from the distal ends of said U-shaped support elements and said end support leg, said tabs being adapted to lie flat against the skin surface, and
    an adhesive material disposed on the tab surface adapted to lie against the skin surface.

5. The incision shield of claim 1 wherein said longitudinal strip and said U-shaped support elements are separate pieces, and
    further including means for securing said U-shaped support elements to said longitudinal strip.

6. The shield of claim 5 wherein said means for securing said plurality of U-shaped support elements along the length of said strip comprises in combination,
    a plurality of annular rings, each defining a snap receptacle through said longitudinal strip, said snap receptacles being aligned in a row along the length of said strip,
    a rounded protrusion extending perpendicularly from the central bar section of each U-shaped structural element adapted to snap into said snap receptacles.

7. The shield of claim 6 wherein said end support leg has a leg section and a bar section, said bar section having a rounded protrusion extending perpendicularly therefrom adapted to snap into engagement within the snap receptacles located at the respective ends of said strip.

8. The shield of claim 7 wherein said means for securing the U-shaped support elements and said end support leg to the skin surface comprises a tab integrally extending from the distal ends of said U-shaped support elements and said end support leg, said tab having a surface adapted to lie on the skin surface, and an adhesive material disposed on the tab surface adapted to lie on the skin surface whereby said tab secures said U-shaped structural elements and said end supports to the skin surface.

9. The shield of claim 8 wherein said annular rings defining said snap receptacles and said rounded protrusions extending perpendicularly from the central bar section of each U-shaped structural element and the bar section of said end support are composed of a class of materials consisting of plastics and metals.

10. The shield of claim 1 wherein said longitudinal strip, said U-shaped support elements and said end support leg are composed of materials from the class consisting of plastic, cardboard, tin and aluminum.

* * * * *